(12) United States Patent
Lerch et al.

(10) Patent No.: US 6,864,381 B2
(45) Date of Patent: Mar. 8, 2005

(54) PROCESS FOR PREPARING ACYLOXYBENZENESULFONATES

(75) Inventors: Alexander Lerch, Gelnhausen (DE); Michael Seebach, Hofheim (DE); Wolf-Dieter Mueller, Charlotte, NC (US)

(73) Assignee: Clariant GmbH, Frankfurt (DE)

( * ) Notice: Subject to any disclaimer, the term of this patent is extended or adjusted under 35 U.S.C. 154(b) by 0 days.

(21) Appl. No.: 10/755,950

(22) Filed: Jan. 13, 2004

(65) Prior Publication Data

US 2004/0198995 A1 Oct. 7, 2004

(30) Foreign Application Priority Data

Jan. 14, 2003 (DE) ................................ 103 00 981

(51) Int. Cl.[7] .............................................. C07B 45/00
(52) U.S. Cl. ......................... 554/90; 560/130; 560/142
(58) Field of Search ............................ 554/90; 560/130, 560/142

(56) References Cited

U.S. PATENT DOCUMENTS

| | | | |
|---|---|---|---|
| 3,503,888 A | 3/1970 | Miller et al. ............... | 252/117 |
| 4,537,724 A | 8/1985 | McKinnie et al. .......... | 260/400 |
| 4,587,054 A | 5/1986 | Hardy et al. .............. | 260/410.2 |
| 4,588,532 A | 5/1986 | Moyne et al. .............. | 260/402 |
| 4,619,779 A | 10/1986 | Hardy ...................... | 252/91 |
| 4,704,236 A | 11/1987 | Sankey et al. ............. | 260/402 |
| 5,069,828 A | 12/1991 | Dumas et al. .............. | 260/402 |
| 5,523,434 A | 6/1996 | Burns et al. ............... | 554/68 |
| 6,448,431 B1 * | 9/2002 | Hembre ..................... | 560/130 |
| 6,639,096 B2 | 11/2003 | Reinhardt et al. .......... | 560/142 |
| 2002/0058824 A1 | 5/2002 | Majerczak et al. ......... | 549/438 |

FOREIGN PATENT DOCUMENTS

| | | |
|---|---|---|
| DE | 0 666 626 | 9/1938 |
| DE | 101 29 663 | 9/2003 |
| EP | 0 098 129 | 1/1984 |
| EP | 0 105 672 | 4/1984 |
| EP | 0 105 673 | 4/1984 |
| EP | 0 125 641 | 11/1984 |
| EP | 0 164 786 | 12/1985 |
| EP | 0 220 826 | 5/1987 |
| WO | WO 01/19771 | 9/2001 |

* cited by examiner

*Primary Examiner*—Deborah D. Carr
(74) *Attorney, Agent, or Firm*—Richard P. Silverman

(57) ABSTRACT

A process for preparing acyloxybenzenesulfonates by reacting a carboxylic acid derivative with a salt of a phenolsulfonic acid in the presence of an antioxidant, preferably 2,6-di-tert-butyl-4-methylphenol. The addition of such antioxidants gives a product having a high color quality.

12 Claims, No Drawings

PROCESS FOR PREPARING ACYLOXYBENZENESULFONATES

The invention relates to a process for preparing acyloxybenzenesulfonates having good color qualities starting from carboxylic acid derivatives and salts of a phenolsulfonic acid in the presence of an antioxidant.

Acyloxybenzenesulfonic acids and their salts are long-established compounds. Depending on the chain length of the acyl group they may find use as surfactants, as bleach activators, or in other applications.

DE 666 626 describes their surfactant properties and their general use in laundry detergents, while compounds having from 6 to 12 carbon atoms in the alkyl chain, in combination with persalts, are claimed as bleaches by EP 98 129, EP 105 672, EP 105 673 and EP 125 641.

For the preparation of acyloxybenzenesulfonic acids and their salts a multiplicity of methods have been described. They can be obtained by heating a mixture of trifluoroacetic anhydride, sodium phenolsulfonate (SPS), and a ($C_6$–$C_{19}$) alkane-carboxylic acid. According to U.S. Pat. No. 4,587,054 this reaction can also be carried out in two stages: first, the alkanecarboxylic acid is converted into the anhydride in the presence of an excess of acetic anhydride, and then the isolated anhydride is reacted with dry phenolsulfonate. This reaction takes place at temperatures from 180 to 220° C. under base catalysis. The acid catalyzed reaction of a relatively long-chain alkanoic anhydride with SPS in an aprotic solvent is claimed in U.S. Pat. No. 4,588,532; the acid catalysis (toluenesulfonic acid and related compounds) allows a reaction regime at just 120° C.

Also known from the literature is the transesterification of ($C_2$–$C_3$)acyloxy-benzenesulfonate with a ($C_6$–$C_8$) alkanecarboxylic acid accompanied by removal of the short-chain alkanecarboxylic acid formed. It is also possible to react alkali metal or alkaline earth metal phenolsulfonates with a $C_2$–$C_{31}$-alkanephenyl ester at from 200 to 350° C.

A further preparation variant is the reaction of aliphatic or aromatic carbonyl halides with salts of phenolsulfonic acid. The reaction can be carried out under Schotten-Baumann conditions in an aqueous system (U.S. Pat. No. 5,523,434), but in that case leads only to moderate conversions. More advantageous is the reaction of anhydrous salts of phenolsulfonic acids in water-free media. Organic solvents such as methylene chloride (U.S. Pat. No. 3,503,888), high-boiling hydrocarbons (EP 220 826), xylene or toluene (EP 164 786), and trifluoroacetic acid (WO 01/19 771) serve as the reaction medium. According to U.S. Pat. No. 5,069,828 this reaction is conducted in an aprotic organic solvent in the presence of a phase transfer catalyst. According to US patent application 20 020 058 824 this reaction can also be conducted solventlessly if an excess of acid chloride is employed.

With all of the known industrially useful processes the problem arises that abovementioned syntheses involve a series of secondary reactions, thereby significantly adversely affecting the color of the end products.

It is an object of the present invention, therefore, to develop a process which can be carried out both industrially and continuously and which leads in very good yields to extremely uniform products which in terms of composition, quality, and color are suitable for use in detergents.

It has surprisingly now been found that acyloxybenzenesulfonates can be prepared in high yields with good color quality if the reaction of a carboxylic acid derivative with the salt of a phenolsulfonic acid takes place in the presence of an antioxidant.

The invention provides a process for preparing acyloxybenzenesulfonates by reacting phenolsulfonates with carboxylic acid derivatives, which comprises carrying out the reaction in the presence of an antioxidant.

The phenolsulfonate starting compounds used are preferably compounds of the formula

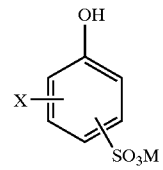

where X is hydrogen, halogen or $C_1$–$C_4$-alkyl and M is an alkali metal or alkaline earth metal ion. Preference is given to sodium ortho- or para-phenolsulfonates, especially sodium para-phenolsulfonate (SPS), which as a result of its preparation process may contain isomeric byproducts (up to 10%) or other impurities in small amounts.

SPS is prepared by sulfonating phenol and then neutralizing the product. Since Na p-phenolsulfonate is of low solubility in water, it can be isolated from the reaction medium by filtration, centrifugation or similar operations. The crude SPS is then washed and after isolation has a high purity and a water content of from 15 to 30%. For the reaction according to the invention with a carboxylic acid derivative it is advantageous to dry the phenolsulfonate to a residual moisture content of <0.5%, preferably <0.2%, by weight. This operation can be carried out continuously or in stages via the dihydrate (water content approximately 15% by weight) and quarter-hydrate (water content approximately 2% by weight). Drying can take place in accordance with conventional methods which are known per se, in a disk drier or fluid-bed drier, for example, which allows drying to a residual moisture content of less than 0.1% by weight. In the course of drying it is advantageous to operate under a stream of inert gas. Drying can be operated under reduced pressure or with the same result under atmospheric pressure as well.

Depending on the equipment used the drying times can be between 1 min and 18 h, the temperatures between 80 and 250° C. For the process of the invention the thermal pretreatment of the dried SPS has no effect on the yield of the acylation reaction and it is possible to obtain on average conversions of more than 95%.

In one preferred embodiment the salt of phenolsulfonic acid treated in accordance with the process described above is contacted prior to acylation with a substance having basic properties.

Suitable substances having basic properties include all organic or inorganic compounds having pKa values <7. Use is made in particular of inorganic bases, such as alkali metal or alkaline earth metal oxides, hydroxides, carbonates, hydrogen carbonates, phosphates, etc. Particular preference is given to sodium carbonate, sodium hydrogen carbonate, and sodium hydroxide, but also to the corresponding K salts.

The bases can be contacted either in anhydrous form, i.e., as powders, slurries or pastes, or as an aqueous solution with the SPS. This can be done directly after the SPS has been isolated, i.e., after the filter cake has been washed, or before or during drying to give the dihydrate or quarter-hydrate. Alternatively, contacting may also take place during subsequent drying to give the anhydrous SPS. The addition may be made both in suitable apparatus, such as mixers, or else directly before or during the drying itself. In this specific case this is done most advantageously either by spraying the dissolved base directly into the drying apparatus or by feeding it continuously in parallel with the moist SPS during the charging of the drier.

The amount of base needed is between 0.01 and 10% by weight, preferably from 0.1 to 5% by weight, based on the SPS in dihydrate form (water content approximately 15% by weight).

As carboxylic acid derivatives it is possible to use both the halides and the anhydrides of the formula

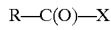

where X=Cl, Br, O—C(O)—R, where R can be $C_1$–$C_{18}$ linear or branched alkyl radicals, the alkyl group being uninterrupted or interrupted, if desired, by an ester group or amide group, or $C_5$–$C_{11}$ aryl radicals, containing, if desired, heteroatoms such as nitrogen and being unsubstituted or substituted.

As carboxylic acid it is possible to use linear or branched, saturated or unsaturated alkanecarboxylic acids having from 1 to 22 carbon atoms. Examples thereof are acetic acid, hexanoic acid, heptanoic acid, octanoic acid, methyloctanoic acid, nonanoic acid, 3,3,5-isononanoic acid, decanoic acid, undecanoic acid, undecenoic acid, lauric acid, myristic acid, hydrogenated tallow fatty acid, stearic acid, benzoic acid or chlorobenzoic acid. Particular preference is given to octanoic acid, nonanoic acid, isononanoic acid, decanoic acid, and lauric acid. The alkanecarboxylic acid may bear further substituents such as halogens, nitro groups or amino groups or may be interrupted by oxygen atoms, ester functions and/or amido functions. Examples thereof are n-octylchloroformic acid, nonylchloroformic acid, octanoyloxyacetal chloride, phthalimidohexanoyl chloride and nonanoylamidohexanoyl chloride.

Particularly suitable are the carbonyl chlorides or bromides, the chlorides being preferred. They may be prepared from the corresponding carboxylic acids, for example, by reaction with phosgene, thionyl chloride, phosphorus trichloride, phosphorus oxychloride, phosphorus pentachloride or phosphorus tribromide.

The anhydrides used may be symmetric or unsymmetric compounds. Examples thereof are acetic anhydride, nonanoic anhydride, isononanoic anhydride, benzoic anhydride, octanoic anhydride or acetylnonanoic anhydride.

Carboxylic acid derivative and phenolsulfonate can be reacted, in accordance with the invention, preferably in a molar ratio of from 0.8:1 to 2:1, preferably from 1:1 to 1.5:1, with one another.

In accordance with the invention one or else two or more antioxidants is or are added to the solution or dispersion of phenolsulfonate prior to acylation with a carboxylic acid derivative.

Particularly suitable are di- and tri-alkyl-phenols, examples being 2,4-di-tert-butylphenol, 2,6-di-tert-butyl-4-methylphenol, 2,4,6-tri-tert-butylphenol, 2,6-di-tert-butyl-4-nonylphenol, 6-tert-butyl-2,4-dimethylphenol,6-tert-butyl-2,4-dimethylphenol, 2,4-dimethyl-6-nonylphenol, 2,4-dimethyl-6-(1-phenylethyl)phenol, 2,4-dimethyl-6-(1-methylcyclohexyl)phenol, 2,6-dimethyloctadecyl-4-methylphenol, di-n-octadecyl(5-tert-butyl-4-hydroxy-3-methylbenzyl)malonate, styreneized phenols, 3,5-di-tert-butyl-4-hydroxybenzyl alcohol, 2,6-di-tert-butyl-4-methoxyphenol, octadecyl 3-(3,5-di-tert-butyl-4-hydroxyphenyl)propionate, pentaerythrityl tetrakis-[3-(3,5-di-tert-butyl-4-hydroxyphenyl)propionate], 1,6-bis[3-(3,5-di-tert-butyl-4-hydroxyphenyl)propionyl]-n-hexane, di-n-octyl 2,2-bis(3,5-di-tert-butyl-4-hydroxybenzyl)malonate, 2,2'-methylenebis(4,6-dimethylphenol), 2,2'-methylenebis (6-tert-butyl-4-methylphenol), 2,2'-methylenebis(4-methyl-6-nonylphenol), 2,2'-methylenebis[4-methyl-6-(1-methylcyclohexyl)phenol], 2,2'-methylenebis[4-ethyl-6-(α-methylbenzyl)phenol], 2,2'-methylenebis(4-ethyl-6-tert-butylphenol), 1,1-bis(2-hydroxy-3,5-dimethylphenyl) butane, 1,1'-methylenebis(naphth-2-ol), 2,2-bis(4-hydroxyphenyl)-propane (Bisphenol A), mixture of tert-butylated 2,2-bis(4-hydroxyphenyl)propane, glycol bis-3,3-bis(4-hydroxy-3-tert-butylphenyl)butanoate, 1,1-bis(5-tert-butyl-4-hydroxy-2-methylphenyl)butane, 1,1,3-tris(5-tert-butyl-4-hydroxy-2-methylphenyl)butane, 4,4'-methylenebis (2-tert-butyl-6-methylphenol), 4,4'-methylenebis(2,6-di-tert-butylphenol), 4,4'-methylenebis(2,5-di-tert-butylphenol), 1,1'-bis(4-hydroxyphenyl)-cyclohexane, 1,1-bis(3-cyclohexyl-4-hydroxyphenyl)cyclohexane, 1,3,5-trimethyl-2,4,6-tris(3,5-di-tert-butyl-4-hydroxybenzyl) benzene, pyrocatechol, 4-tert-butylpyrocatechol, hydroquinone, 4-methoxyphenol, 4-benzyloxyphenol, mixtures of 2- and 3-tert-butyl-4-hydroxyanisole (BHA), 2,6-di-tert-butyl-4-methoxyphenol, 3,5-di-tert-butyl-4-hydroxyanisole, 2,5-di-tert-butylhydroquinone (DBH), 2,5-bis(1,1-dimethyl-propyl)hydroquinone, tocopherols, nordihydroguaiaretic acid, α- and β-naphthol, 6,7-dihydroxy-4-methylcoumarin, 5,7-dihydroxy-4-methylcoumarin monohydrate, 1,3,5-trihydroxybenzene, propyl 3,4,5-trihydroxybenzoate, octyl 2,4,5-trihydroxybenzoate, dodecyl 3,4,5-trihydroxybenzoate, and 2,4,5-trihydroxybutyrophenone.

Also suitable are antioxidants from the group of the amines, examples being N,N'-di-isopropyl-p-phenylenediamine, N,N'-di-sec-butyl-p-phenylenediamine, N,N'-bis(1,4-dimethylphenyl)-p-phenylenediamine, N,N'-bis(1-ethyl-3-methylpentyl)-p-phenylenediamine, N,N'-bis (1-methylheptyl)-p-phenylenediamine, N,N'-dicyclohexyl-p-phenylenediamine, N,N'-diphenyl-p-phenylenediamine, N,N'-di-(naphthyl-2)-p-phenylenediamine, N-isopropyl-N'-phenyl-p-phenylenediamine, N-(1,3-dimethyl-butyl)-N'-phenyl-p-phenylenediamine, N-(1-methylheptyl)-N'-phenyl-p-phenylenediamine, N-cyclohexyl-N'-phenyl-p-phenylenediamine, 4-(p-toluenesulfonamido)-diphenylamine, N,N'-dimethyl-N,N'-di-sec-butyl-p-phenylenediamine, diphenylamine, 4-isopropoxydiphenylamine, N-phenyl-1-naphthylamine, N-phenyl-2-naphthylamine, 4-n-butylaminophenol, 4-butyraminophenol, 4-nonaroylaminophenol, 4-dodecanoylaminophenol, 4-octadecanoylaminophenol, di-(4-methoxyphenyl)amine, 2,6-di-tert-butyl-4-dimethylaminomethylphenol, 2,4'-diaminodiphenylmethane, 4,4'-diamino-diphenylmethane, N,N,N',N'-tetramethyl-4,4'-diaminodophenylmethane, 1,2-di-(phenylamino)ethane, 1,2-di-[(2-methylphenyl)amino] ethane, 1,3-di-(phenylamino)propane, (o-tolyl) biguanide, N,N'-disalicylidene-1,2-propanediamine, oxalylbis-(benzylidenehydrazide), ethylenediaminetetraacetic acid (EDTA), ethylenediamine-N,N'-disuccinic acid (EDDA), N-hydroxyethylenediaminetriacetic acid, nitrilotriacetic acid, ethylenediaminetetrapropionic acid, ethylenediamine-N,N'-diglutamic acid, 2-hydroxypropylenediamine-N,N'-disuccinic acid, triethylenetriaminehexaacetic acid, diethylenetriaminepentaacetic acid, trans-1,2-diaminocyclohexane-N,N,N',N'-tetraacetic acid, condensation product of aniline and acetaldehyde, aniline-aldol condensate, product of aniline and butyraldehyde, polymeric 2,2,4-trimethyl-1,2-dihydroquinoline, aniline-acetone condensate, 6-ethoxy-2,2, 4-trimethyl-1,2-dihydro-quinoline, 6-dodecyl-2,2,4-trimethyl-1,2-dihydroquinoline, 2,2,4-trimethyl-6-phenyl-1, 2-dihydroquinoline, 1-aminonaphthalene-aldol condensate, product of 2-phenylaminonaphthalene and acetone, diphenylamine-acetone condensate, 3,5-dimethylacridan, aromatic amine-aliphatic ketone condensate, phenol-aldehyde-amine condensation product, 3,3'-thiodipropionic acid, 3,3'-thiobis(dodecyl propionate), dilauryl thiodipropionate, 3,3'-thiobis(tridecyl propionate), 3,3'-thiobis(tetradecyl propionate), 3,3'-thiobis(octadecyl propionate), 2,2'-thiobis(6-methylphenol), 2,2'-thiobis(4-methyl-6-tert-butylphenol), 4,4'-thiobis(2-methyl-6-tert-butylphenol), 4,4'-thiobis(2-tert-butyl-5-methylphenol), 1,1'-thiobis(naphth-2-ol), 2-mercaptobenzimidazole, zinc salt of 2-mercaptobenzimidazole, phenothiazine and alkyl derivatives, nickel N,N'-dibutyldithiocarbamate, N,N'-diethylthiourea, N,N'-dibutylthiourea, bis-(3-thiapentadecanyl) and bis(3,5-di-tert-butyl-4-hydroxybenzyl)malonate.

Likewise suitable as antioxidants are phosphorus compounds. Those suitable include triphenylphosphine, diethyl phosphite, triphenyl phosphite, trisnonylphenyl phosphite, tris(mono-/di-nonylphenyl) phosphite, tridecyl phosphite, triisodecyl phosphite, tridodecyl phosphite, condensation product of 4,4'-thiobis(2-tert-butyl-5-methylphenol), octyl diphenyl phosphite, isooctyl diphenyl phosphite, decyl diphenyl phosphite, isodecyl diphenyl phosphite, didecyl phenyl phosphite, diisodecyl phenyl phosphite, diethyl 3,5-di-tert-butyl-4-hydroxybenzylphosphonate, and di-n-octadecyl 3,5-di-tert-butyl-4-hydroxybenzylphosphonate.

Additionally suitable are L(+)-ascorbic acid, 5,6-diacetyl-L(+)-ascorbic acid, 6-palmityl-L(+)-ascorbic acid, propyl gallate, dodecyl gallate, citric acid, 2-(3,5-di-tert-butyl-4-hydroxyanilino)-4,6-bis-(n-octylthio)-1,3,5-triazine, 1,4-dimethoxybenzene, 1,4-diethoxybenzene, 2-butanone oxime, organotin compounds, ethanoldiglycine, ethylenediaminetetrakismethylenephosphonic acid, 1-hydroxyethane-1,1-diphosphonic acid, hydroxyethanedimethylenephosphonic acid, and sodium dithiocarbamate.

Antioxidants particularly preferred in accordance with the invention for preparing acyloxybenzenesulfonate with good color quality are 2,6-di-tert-butyl-4-methyl-phenol (BHT), tetrakis[methylene(3,5-di-tert-butylhydroxyhydrocinnamate)]methane (Hostanox® 010), octadecyl 3,5-di-tert-butyl-4-hydroxyhydrocinnamate (Hostanox 016), tris(2,4-di-tert-butylphenyl)phosphite (Hostanox PAR24), mixtures of Hostanox 010 and Hostanox PAR24 (mixing ratio 1:2, Hostanox M102), Hostanox 016 and Hostanox PAR24 (mixing ratio 1:2, Hostanox M108 or mixing ratio 1:4, Hostanox M105), but also 1,3,5-tris-(3,5-di-tert-butyl-4-hydroxybenzyl)-[1,3,5]triazine-2,4,6 (Hostanox 014), thiodiethylenebis(3,5-di-tert-butyl-4-hydroxyhydrocinnamate), N,N'-hexamethylenebis(3,5-di-tert-butyl-4-hydroxyhydrocinnamide), calcium bis[monoethyl(3,5-di-tert-butyl-4-hydroxybenzyl)phosphonate], and 1,3,5-tris(3,5-di-tert-butyl-4-hydroxybenzyl)-s-triazine-2,4,6-(1H,3H,5H)trione.

The antioxidants are added in amounts of from 5 ppm to 1 000 ppm, preferably from 50 ppm to 500 ppm, and more preferably from 100 ppm to 300 ppm to the reaction mixture or to the individual reactants at room temperature or else at elevated temperatures and/or reaction temperature.

The acylation may be conducted in common protic or aprotic solvents or in an excess of the corresponding acid. Particularly preferred as reaction medium are aliphatic or aromatic hydrocarbons having boiling points of between 80 and 200° C., in particular from 100 to 180° C., examples being toluene, xylene, paraffins having from 8 to 22 carbon atoms, such as decane, undecane, dodecane, hexadecane or octadecane, or mixtures thereof. Particularly suitable are aliphatic hydrocarbon mixtures such as are available commercially as Shellsols (Shell), ISOPAR G and ISOPAR 4 (ESSO). The solubility of the SPS in this reaction medium is frequently below 1%.

An additional catalyst is normally not necessary but may offer advantages in certain cases. Preference is given to open-chain or cyclic tertiary amines or carboxamides (as described in DE 101 29 663.5), phase transfer catalysts or acidic catalysts such as p-toluenesulfonic acid. The molar ratio of the catalyst used to the phenolsulfonate is from 0.0001:1 to 0.02:1, preferably from 0.005:1 to 0.012:1.

The acylation reaction is conducted at temperatures between 60 and 200° C., in particular between 100 and 150° C. The gas formed during the reaction is taken off; if desired, the reaction is blanketed with an inert stream of nitrogen or argon gas. The reaction is conducted as a heterogeneous reaction (slurry), since neither the phenolsulfonate nor the acyloxybenzenesulfonate product have any notable solubility in the reaction medium. The reaction time is guided by the reaction conditions and may amount to between 10 min and 5 h, preferably from 30 to 120 min.

In one particular embodiment the reaction of the invention can be conducted continuously. Particularly suitable for this purpose are tank cascades and/or tubular reactors, such as are known to the skilled worker.

After the end of reaction, the reaction product is isolated by conventional separation methods. Centrifuges and filter apparatus are suitable for this purpose. For complete separation of the catalyst it is advisable to wash the solid reaction product with the reaction medium one or more times. The mother liquor can be used without further purification for the subsequent reactions, or cycled. The acyloxybenzenesulfonate formed is obtained in high yields in the form of a white powder that can be isolated by conventional drying.

The acyloxybenzenesulfonates prepared by the process described above in the presence of antioxidants feature a significantly better color quality in comparison to products synthesized in the absence of antioxidants.

EXAMPLES

Synthesis Method I (Without BHT)

98.1 g (0.5 mol) of Na p-phenolsulfonate, (dried at 130° C./50 mbar for 16 h, treated with NaHCO$_3$) were introduced in 146.77 g of Isopar G (aliphatic hydrocarbon) and heated to 140° C. Over the course of 30 minutes 114.9 g (0.65 mol) of nonanoyl chloride were added dropwise at 140° C., after which the mixture was stirred at 140° C. for 2 h and cooled to 80° C. The solid was filtered off with suction on a Büchner funnel (Pannevis) at 600 mmHg and washed with 84 g of Isopar G and the solvent was removed under reduced pressure. The filter cake was dried on a rotary evaporator at 200° C. and 50 mbar for a period of 10 minutes or 20 minutes.

Synthesis Method II (With Antioxidants)

98.1 g (0.5 mol) of sodium p-phenolsulfonate (dried at 130° C./50 mbar for 16 h, treated with NaHCO$_3$) in 146.77 g of Isopar G (aliphatic hydrocarbon) and 3.43 g (corresponding to 250 ppm BHT) of a solution of 1.2607 g of 2,6-di-tert.-butyl-4-methylphenol, (BHT) in 46.2418 g of Isopar G) were introduced as an initial charge and heated to 140° C. Over the course of 30 minutes 114.9 g (0.65 mol) of nonanoyl chloride were added dropwise at 140° C. and the mixture was subsequently stirred at 140° C. for 2 h and cooled to 80° C. The solid was filtered off with suction on a Büchner funnel (Pannevis) at 600 mmHg and washed with 84 g of Isopar G and the solvent was removed under reduced pressure. The filter cake was dried on a rotary evaporator at 200° C. and 50 mbar for a period of 10 minutes or 20 minutes.

Nonanoyloxybenzenesulfonate was prepared analogously with the antioxidants tetrakis[methylene(3,5-di-tert-butylhydroxyhydrocinnamate)]methane (Hostanox 010), octadecyl 3,5-di-tert-butyl-4-hydroxyhydrocinnamate (Hostanox 016), tris(2,4-di-tert-butylphenyl)phosphite (Hostanox PAR24), mixtures of Hostanox 010 and Hostanox PAR24 (mixing ratio 1:2, Hostanox M102), Hostanox 016 and Hostanox PAR24 (mixing ratio 1:2, Hostanox M108 or mixing ratio 1:4, Hostanox M105), but also 1,3,5-tris-(3,5-di-tert-butyl-4-hydroxybenzyl)-[1,3,5]triazine-2,4,6-trione (Hostanox 014), using antioxidant amounts of 200 ppm and 400 ppm.

The color quality was determined on the basis of the Hazen color number by means of a LICO 300 colorimeter in accordance with DIN 53995. The values measured were as follows:

| Synthesis method | Drying time [min] | Hazen color number [mg Pt/min] |
|---|---|---|
| I (without BHT) | 10 | 63 |
| I (without BHT) | 20 | 61 |
| II (with BHT) | 10 | 37 |
| II (with BHT) | 20 | 40 |

| NOBS with antioxidant | Amount of antioxidant ppm | Hazen color number [mg Pt/min] |
|---|---|---|
| Hostanox M108 | 200 | 48 |
| Hostanox M108 | 400 | 27 |
| Hostanox M105 | 200 | 41 |
| Hostanox M105 | 400 | 27 |
| Hostanox M102 | 200 | 44 |
| Hostanox M102 | 400 | 34 |
| Hostanox M 016 | 200 | 54 |
| Hostanox M 016 | 400 | 49 |
| Hostanox M 010 | 200 | 47 |
| Hostanox M 010 | 400 | 43 |
| Hostanox M 014 | 200 | 51 |
| Hostanox M 014 | 400 | 44 |

These color number values show that by adding antioxidants in accordance with the present invention products are obtained which contain a substantially lower amount of colored impurities in comparison to such products in whose preparation no antioxidants are used.

The acyloxybenzenesulfonate obtained in this way can be used as a surfactant or persalt activator in detergents such as powder-form heavy-duty laundry detergents, scouring salts or powder-form dishwasher detergents. In order to increase the storage stability in these formulations the acyloxybenzenesulfonate can be converted, as the skilled worker is aware, into a granular form.

What is claimed is:

1. A process for preparing acyloxybenzenesulfonates by reacting a carboxylic acid derivative with a salt of a phenolsulfonic acid in the presence of an antioxidant.

2. The process as claimed in claim 1, wherein a di- or tri-alkylphenol is used as antioxidant.

3. The process as claimed in claim 1, wherein 2,6-di-tert-butyl-4-methylphenol, tetrakis[methylene(3,5-di-tert-butylhydroxyhydrocinnamate)]methane, octadecyl 3,5-di-tert-butyl-4-hydroxyhydrocinnamate, tris(2,4-di-tert-butylphenyl) phosphite, 1,3,5-tris-(3,5-di-tert-butyl-4-hydroxybenzyl)-[1,3,5]triazine-2,4,6-trione, thiodiethylenebis(3,5-di-tert-butyl-4-hydroxyhydrocinnamate), N,N'-hexamethylenebis-(3,5-di-tert-butyl-4-hydroxyhydrocinnamide), calcium bis[monoethyl(3,5-di-tert-butyl-4-hydroxybenzyl) phosphonate] or 1,3,5-tris(3,5-di-tert-butyl-4-hydroxybenzyl)-s-triazifle-2,4,6-(1H,3H,5H)trione is used as antioxidant.

4. The process as claimed in claim 1, wherein the antioxidant is used in amounts of from 5 ppm to 1,000 ppm.

5. The process as claimed in claim 1, wherein the antioxidants are added to the individual reactants or to the reaction mixture.

6. The process as claimed in claim 1, wherein the reaction is conducted with a salt of a phenolsulfonic acid which has a water content of less than 0.5% by weight.

7. The process as claimed in claim 1, wherein the reaction is conducted with a salt of a phenolsulfonic acid which has a water content of less than 0.2% by weight.

8. The process as claimed in claim 1, wherein the salt of the phenolsulfonic acid is contacted, prior to the reaction with the carboxylic acid derivative, with a substance having basic properties which has a pKa of less than 7.

9. A process for preparing acyloxybenzenesulfonates comprising the steps of:

providing a phenolsulfonates of the formula

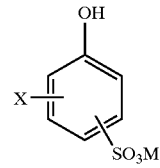

where X is hydrogen, halogen or $C_1$–$C_4$-alkyl and M is an alkali metal or alkaline earth metal ion;

providing a carboxylic acid derivatives of the formula

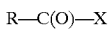

where X=Cl, Br, O—C(O)—R, where R can be $C_1$–$C_{18}$ linear or branched alkyl radicals, the alkyl group being uninterrupted or interrupted by an ester group or amide group, or $C_5$–$C_{11}$ aryl radicals, the alkyl group may contain heteroatoms and be unsubstituted or substituted;

providing an antioxidants selected from the group consisting of: 2,6-di-tert-butyl-4-methylphenol, tetrakis[methylene(3,5-di-tert-butylhydroxyhydrocinnamate)] methane, octadecyl 3,5-di-tert-butyl-4-hydroxyhydrocinnamate, tris(2,4-di-tert-butylphenyl) phosphite, 1,3,5-tris-(3,5-di-tert-butyl-4-hydroxybenzyl)-[1,3,5]triazine-2,4,6-trione, thiodiethylenebis(3,5-di-tert-butyl-4-hydroxyhydrocinnamate), N,N'-hexamethylenebis-(3,5-di-tert-butyl-4-hydroxyhydrocinnamamide), calcium bis[monoethyl(3,5-di-tert-butyl-4-hydroxybenzyl) phosphonate], 1,3,5-tris(3,5-di-tert-butyl-4-hydroxybenzyl)-s-triazine-2,4,6-(1H,3H,5H)trione and combinations thereof:

reacting said phenolsulfonates with said carboxylic acid derivatives in the presence of said antioxidants, where said antioxidants are used in amounts of from 5 ppm to 1,000 ppm.

10. The process as claimed in claim 4, wherein the antioxidant is used in amounts of from 50 ppm to 500 ppm.

11. The process as claimed in claim 4, wherein the antioxidant is used in amounts of from 100 ppm to 300 ppm.

12. The process as claimed in claim 1, where the antioxidant is 2,6-di-tert-butyl-4-methylphenol.

* * * * *